United States Patent [19]

Motes

[11] 4,170,591
[45] Oct. 9, 1979

[54] AZIRIDINE COMPLEXES ISOMERIZE TO FORM CHELATED DIMERS

[75] Inventor: John M. Motes, Lake Jackson, Tex.

[73] Assignee: The Dow Chemical Company, Midland, Mich.

[21] Appl. No.: 358,564

[22] Filed: May 9, 1973

Related U.S. Application Data

[63] Continuation of Ser. No. 128,128, Mar. 25, 1971, abandoned, which is a continuation-in-part of Ser. No. 731,613, May 23, 1968, abandoned.

[51] Int. Cl.$^2$ .................... C07D 203/12; A01N 9/22
[52] U.S. Cl. .................................. 260/239 E; 71/88
[58] Field of Search .................... 260/239 E

[56] References Cited

PUBLICATIONS

Root et al., A.C.S. Abs. of Papers, 156th Meeting (1968), Abstract INOR 145.
Jackson et al., J.A.C.S. 83, 355–360 (1961).
Jackson et al., Inorg. Chem. 1, 398–401 (1962).
Kiser et al., Inorg. Chem. 1, 401–404 (1968).
Patai, "The Chemistry of the Hydroxyl Groups" (Interscience Publishers, 1971), p. 369.
Takemoto et al., Chem. Abs. 72, 83379r (1970).
Cotton et al., Advanced Inorg. Chem., 2nd Ed. Interscience Publishers, p. 826.

*Primary Examiner*—Mark L. Berch
*Attorney, Agent, or Firm*—L. Wayne White; J. P. Hill

[57] ABSTRACT

Metal salt complexes of aziridine and 2-alkylaziridines in solution isomerize at temperatures between 20°–70° C. to form aziridine dimer chelates. The chelates are biologically active compounds and are chemical intermediates in the preparation of free aziridine dimers.

16 Claims, No Drawings

AZIRIDINE COMPLEXES ISOMERIZE TO FORM CHELATED DIMERS

RELATED APPLICATIONS

This is a continuation of application, Ser. No. 128,128, abandoned, filed Mar. 25, 1971, which is a CIP application of Ser. No. 731,613, filed May 23, 1968 and now abandoned.

BACKGROUND OF THE INVENTION

1. Field of the Invention
Aziridine-metal chelated compounds.
2. Description of the Prior Art
References
1. T. B. Jackson and J. O. Edwards, J. Am. Chem. Soc., 83, 355 (1961).
2. T. B. Jackson and J. O. Edwards, Inorg. Chem., 1, No. 2, 398 (1962).
3. R. W. Kiser and T. W. Lapp, Inorg. Chem., 1, No. 2, 401 (1962).

The above references indicate that stable complexes are formed between aziridine and certain metal ions. The maximum coordination number of the metal ion and the strength of the metal-nitrogen bond is substantially the same as for the corresponding amine complexes in most cases. Any lowering of the coordination number was attributed to steric effects provided by the aziridine ring; the steric properties of aziridine are cited as intermediate to methylamine and ethylamine.

The method of preparing the metal-aziridine complexes is taught in reference 1 above.

The complexes were stable against aging, and aziridine was lost only from those complexes containing the chloride anion. No ring opening was observed during the stability testing and it was concluded that the presence of a metal ion did not cause a significantly more rapid ring opening.

SUMMARY OF THE INVENTION

It has now been discovered that aziridine-metal salt complexes, of the formula

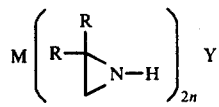

in solution undergo a ring opening reaction to form compounds of the general formula:

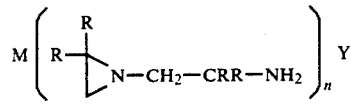

wherein R is hydrogen or an alkyl radical of from 1 to about 4 carbon atoms and wherein n=2 or 3, and wherein M and Y are as described below. The compounds are stable chelates, solids, purified typically by recrystallization, and produced in high yields.

Suitable cations, M, for the metal salts are the divalent and trivalent ions of Cr, Mn, Fe, Co, Ni, Cu and Zn with the preferred species being ions of Co, Ni, Cu and Zn.

Y is n equivalents of a neutralizing anion and is essentially inert in the process. Suitable such anions include halides, sulfate, bisulfate, perchlorate, nitrate, formate, acetate, benzoate, tosylate, methyl sulfonate ($CH_3SO_3^-$), methyl sulfate ($CH_3O-SO_3^-$) and the like. Preferred anions are chloro, bromo, sulfate, nitrate, and acetate.

Thus, representative salts include combinations of the above mentioned cations and anions, e.g., $CrBr_2$, $CrCl_3$, $MnCl_2$, $FeCl_3$, $FeCl_2$, $Fe(acetate)_2$, $CuF_2$, $CuCl_2$, $CuBr_2$, $CuI_2$, $Cu(NO_3)_2$, $CuSO_4$, $Cu(acetate)_2$, $Cu(ClO_4)_2$, $ZnCl_2$, $ZnBr_2$, $ZnSO_4$, $Zn(NO_3)_2$, $NiCl_2$, $NiBr_2$, $NiSO_4$, $CoF_3$, $CoCl_3$, $CoBr_3$, $Co(acetate)_3$, $Co(NO_3)_2 \cdot 6H_2O$ and other similar combinations of the above named anions and cations. The salts may be used either in an anhydrous or hydrated condition.

Suitable solvents are polar solvents. Preferred solvents are water, alcohols containing 1-4 carbon atoms, dimethylformamide, dimethyl sulfoxide or mixtures of said solvents. Alcohols of higher molecular weight are not particularly effective as solvents for the aziridine-metal salt complexes.

The reaction is effected by preparing an aziridine-metal salt complex solution and adjusting the temperature of said solution to between about 20° and about 70° C. (preferably between 50°–65° C.) and maintaining said temperature for a time sufficient to convert the salt to the dimer chelate. At the lower temperatures the reaction rate is low. At temperatures above about 70° C. one observes an increasing amount of polymerization in addition to the desired formation of the amine dimer chelate.

The amine dimer may be isolated from the chelate structure by reacting a solution of the latter with NaOH. The complexing metal ion precipitates from solution as the hydroxide or oxide and the amine dimer may then be readily separated in high yield.

SPECIFIC EMBODIMENT

The following examples are used to further illustrate the invention but are not intended to limit the scope in any way.

EXAMPLE 1

Preparation of bis(N-2-aminoethylaziridine) copper (II) chloride.

A standard solution was prepared by dissolving anhydrous copper (II) chloride in methanol to a concentration of 0.0015 grams of $CuCl_2$/ml. of solution. A complex, tetraethylenimine copper (II) chloride, was prepared by adding 1 ml. of the standard solution at 0° C. with stirring to a large excess of aziridine (5.0 ml.). The colored precipitate thus formed was filtered under a vacuum and dried in a desiccator which contained solid KOH. A solution comprising 0.5 g. of the above tetraethylenimine copper (II) chloride complex and 25 ml. of methanol was heated 6 hours at 65° C. in a 100 ml. sealed bottle. The reaction mixture was cooled to room temperature and the solvent was removed under reduced pressure. The crystalline solid was dried in a desiccator which contained solid KOH. Melting point 164°–165° C. Analytical data are presented in Table I.

TABLE I

| Elemental Analysis | | | Infrared Spectra | Visible Spectra |
|---|---|---|---|---|
| % C | % H | % N | cm.$^{-1}$ IR | mm. vis. |
| found | | | | |
| 28.15 | 7.54 | 15.89 | 1270, 3060 | 566 |

TABLE I-continued

| | Elemental Analysis | | Infrared Spectra | Visible Spectra |
|---|---|---|---|---|
| % C | % H | % N | cm.$^{-1}$ IR | mm. vis. |
| calc. | | | | |
| 28.03 | 7.06 | 16.53 | | |

Further treatment of a methyl alcohol solution of the above chelate with NaOH gave free

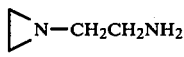

in approximately 95% overall reaction yield.

EXAMPLE 2

The nickel chelate compound was prepared via the procedure of Example 1 except Ni(NO$_3$)$_2$ replaced CuCl$_2$ as the complexing metal salt. Melting point 217°–219° C. (decomposition).

TABLE II

| Ni(AEA)$_2$(NO$_3$)$_2$ . H$_2$O - Elemental Analysis | | | |
|---|---|---|---|
| | % C | % H | % N |
| found | 31.23 | 7.04 | 24.42 |
| calculated | 31.39 | 7.02 | 24.41 |

The following chelates were prepared in substantially the procedure of Example 1 and using the corresponding metal salt: (1) Cu(AEA)$_2$Cl$_2$.2H$_2$O in Example 1, (2) Cu(AEA)$_2$Br$_2$, (3) Cu(AEA)$_2$(NO$_3$)$_2$, (4) Cu(AEA)$_2$SO$_4$, (5) Zn(AEA)$_2$Cl$_2$, (6) Zn(AEA)$_2$(NO$_3$)$_2$, (7) Zn(AEA)$_2$SO$_4$, (8) Ni(AEA)$_2$Cl$_2$, (9) Ni(AEA)$_2$Br$_2$, (10) Ni(AEA)$_2$(NO$_3$)$_2$.H$_2$O in Example 2, wherein AEA above is N-2-aminoethylaziridine.

The chelates of this invention are biologically active compounds and are useful as chemical intermediates in the preparation of aziridine dimers. E.g. (a) Cu(AEA)$_2$Br$_2$, Ni(AEA)$_2$Br$_2$, Cu(AEA)$_2$Cl$_2$, Ni(AEA)$_2$Cl$_2$, and Cu(AEA)$_2$(NO$_3$)$_2$ each individually applied as the sole insecticide at 500 parts per million (p.p.m.) as a spray kills the Southern Army Worm (b) Ni(AEA)$_2$Br$_2$ and Ni(AEA)$_2$(NO$_3$)$_2$ each individually applied as the sole herbicide at 0.4% as a spray kills Spiny Clotbur (c) Cu(AEA)$_2$Br$_2$ and Ni(AEA)$_2$(NO$_3$)$_2$ each individually applied as the sole herbicide at 0.4% kills Yellow Foxtail (d) Cu(AEA)$_2$(NO$_3$)$_2$ applied at 0.4% as a spray prevents and kills Bean Mildew.

Further reacting the chelated aziridine dimer with a base, such as NaOH, is a method of producing the free aminoalkylaziridine, substantially free from other isomers and homologs, in high yields. These aziridines, which contain a primary nitrogen and an aziridine ring, are versatile chemicals which are useful as (a) monomers to make N-substituted polyalkylenimine polymers, which are flocculants, (b) bases to neutralize acids (c) accelerators in the curing and vulcanizing of elastomers, such as epoxy compounds, styrene-butadiene, etc., and other utilities obvious to one skilled in the art.

I claim:

1. A substantially pure and crystalline compound of the formula:

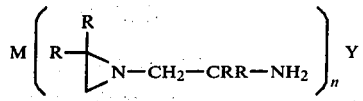

wherein M is an n-valent ion of Co, Ni, Cu or Zn; Y is n equivalents of an anion selected from the group consisting of fluoride, chloride, bromide, iodide, sulfate, nitrate perchlorate and acetate; each R independently is hydrogen or an alkyl radical of from 1 to 4 carbon atoms and n is 2 or 3, being the valence of M.

2. A process for preparing an aziridine-dimer chelate of the formula

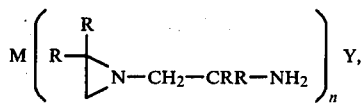

wherein M is an n-valent ion of Cr, Mn, Fe, Co, Ni, Cu or Zn; Y is n-equivalents of an inert anion; each R independently is hydrogen or an alkyl radical of from 1 to 4 carbon atoms; and n is 2 or 3, being the valence of M, said process comprising maintaining a solution of an aziridine-metal salt dissolved in a polar solvent at a temperature of from about 20° to about 70° C. for a time sufficient to convert the aziridine-metal salt to the aziridine-dimer chelate; said aziridine-metal salt corresponding to the formula

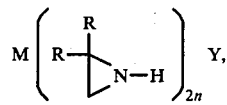

wherein M, R, Y and n have the aforesaid meaning.

3. The compound of claim 1 wherein Y is chloride, bromide, nitrate, sulfate or acetate.

4. The compound of claim 1 wherein each R is hydrogen.

5. The process defined in claim 2 wherein the product is further reacted with NaOH to produce the free aziridine dimer.

6. The process defined in claim 5 wherein the solvent is an alcohol containing 1-4 carbon atoms, water, dimethyl sulfoxide, dimethylformamide, or a mixture of said solvents.

7. The process defined in claim 2 wherein M is Co, Ni, Cu or Zn.

8. The process defined in claim 7 wherein Y is fluoride, chloride, bromide, iodide, nitrate, sulfate, perchlorate or acetate.

9. The process defined in claim 8 wherein the reaction solvent is water, methyl alcohol, ethyl alcohol, dimethyl sulfoxide, or dimethylformamide, or a mixture of said solvents.

10. The process defined in claim 9 wherein said temperature is from 50°–65° C.

11. The compound of claim 4 wherein M is Cu, Y is chloride and n is 2.

12. The process defined in claim 2 wherein said temperature is 50°–65° C.

13. The process defined in claim 2 wherein the reaction solvent is water, an alcohol containing 1-4 carbon atoms, dimethylformamide, dimethylsulfoxide, or a mixture of said solvents.

14. The process defined in claim 13 wherein the process comprises the additional step of removing the solvent under reduced pressure to thereby precipitate the aziridine-dimer chelate as a crystalline solid.

15. The process defined in claim 10 wherein M is Cu, Y is chloride and n is 2.

16. The process defined in claim 15 wherein the process comprises the additional step of removing the solvent under reduced pressure to thereby precipitate the aziridine-dimer chelate as a crystalline solid.

* * * * *